(12) United States Patent
Williams

(10) Patent No.: US 11,179,232 B2
(45) Date of Patent: Nov. 23, 2021

(54) DUAL USE EXERCISE WHITENER APPLIANCE

(71) Applicant: Edward D. Williams, Philadelphia, PA (US)

(72) Inventor: Edward D. Williams, Philadelphia, PA (US)

(*) Notice: Subject to any disclaimer, the term of this patent is extended or adjusted under 35 U.S.C. 154(b) by 0 days.

(21) Appl. No.: 16/353,040

(22) Filed: Mar. 14, 2019

(65) Prior Publication Data

US 2020/0015949 A1   Jan. 16, 2020

Related U.S. Application Data

(63) Continuation of application No. 13/136,280, filed on Jul. 29, 2011, now abandoned.

(51) Int. Cl.
| | | |
|---|---|---|
| *A61C 19/06* | (2006.01) | |
| *A63B 71/08* | (2006.01) | |
| *A61F 5/56* | (2006.01) | |

(52) U.S. Cl.
CPC ............ *A61C 19/066* (2013.01); *A61F 5/566* (2013.01); *A63B 71/085* (2013.01); *A61F 2005/563* (2013.01)

(58) Field of Classification Search
CPC ...... A61F 5/56; A61F 5/566; A61F 2005/563; A61M 16/0488; A61C 19/06; A61C 19/063; A61C 19/066; A61C 7/08; A63B 71/085; A63B 2071/086

USPC ........ 128/848, 857, 859–862; 433/6, 37, 80, 433/215; 602/902

See application file for complete search history.

(56) References Cited

U.S. PATENT DOCUMENTS

| | | | | |
|---|---|---|---|---|
| 5,636,379 A | * | 6/1997 | Williams | ............. A63B 71/085 |
| | | | | 128/862 |
| 7,328,706 B2 | * | 2/2008 | Bardach | ................ A61J 7/0053 |
| | | | | 128/861 |

* cited by examiner

*Primary Examiner* — Keri J Nelson
(74) *Attorney, Agent, or Firm* — Fox Rothschild LLP

(57) ABSTRACT

A jaw-joint protective device is provided for, whitening and brightening a wearer's teeth while protecting the teeth, tongue, lips, jaw, and other delicate structures of the vital cranial triad (VCT) from injury and/or for supporting the condyle of the temporomandibular joint (TMJ) in a relatively fixed (stable) position thereby stabilizing the jaw and the VCT during head contact activity, exercise, physical rehabilitation, C-force acceleration, teeth grinding disorders and sleep apnea and or permit the components of a VCT disorder to be realigned for proper healing. This device is an over-the-counter purchased, boil and bite device for whitening at least one tooth while protecting the jaw-joint, providing maxillary and mandibular teeth seats for protection of the mouth and/or healing of the VCT. This invention provides a device for customized fitting that is purchased over-the-counter that is versatile for protecting not only the mouth but also a larger area, the vital cranial triad which includes the TMJ, while at the same time allows for audible speech, reduces sleep disorders of snoring, grinding and clenching of teeth with additional benefits.

19 Claims, 5 Drawing Sheets

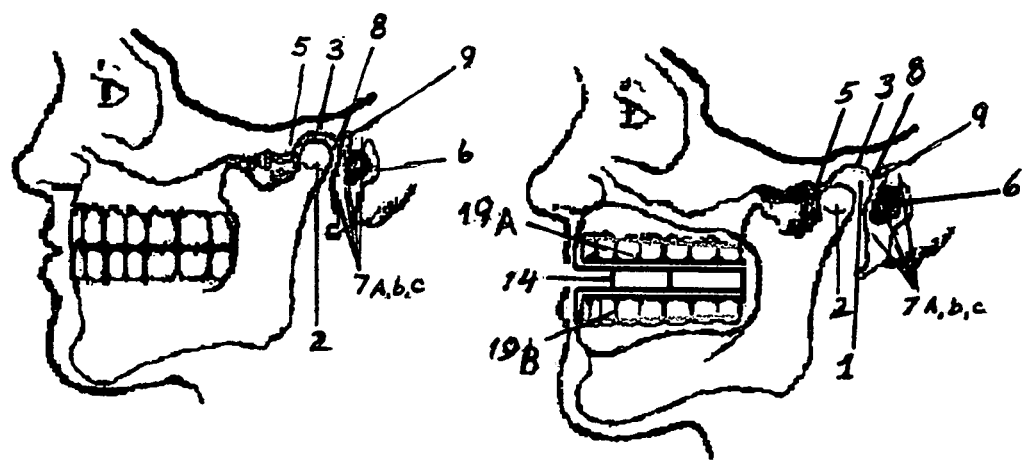
Fig. 1
Fig. 2
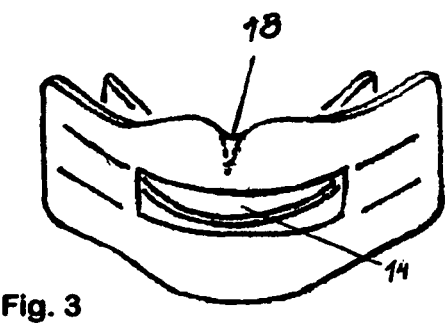
Fig. 3
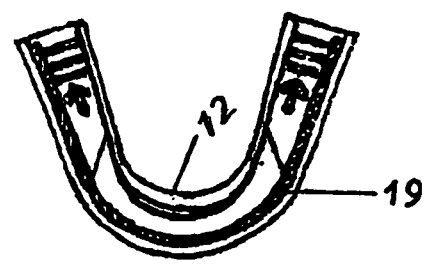
Fig. 4

DUAL USE EXERCISE WHITENER APPLIANCE

CROSS REFERENCE TO RELATED APPLICATION

This application is a continuation of U.S. application Ser. No. 13/136,280, filed Jul. 29, 2011, which is herein incorporated by reference in its entirety.

FIELD OF INVENTION

This invention relates to a dual function protective device that not only protects the oral cavity especially the teeth while exercising and, or engaging in sports but also whitens or brightens the teeth while wearing the device. More particularly, this invention will support and protect the teeth, jaw joint structures, and facial muscles, while whitening the teeth during physical events (e.g., exercise, fitness, physical training, rehabilitation, playing, sleeping and military maneuvers).

BACKGROUND OF THE INVENTION

In the prior art, one method for whitening teeth is to use plastic strips that are impregnated with a whitening agent and are adhered to the teeth. The manufacturer says that they can be worn at any time during the day or even at night when sleeping. Another method of whitening teeth is to use whitening appliances composed of two individual and separate custom fitted bleaching trays bought over the counter or fitted by the dentist. These non-articulated separate and individual trays are placed on the upper (maxillary) and lower (mandibular) teeth respectively. The frequency of use and time of wear for the individual bleaching tray is directly related to the concentration and type of whitening agent and the individual's desired shade of the color change.

The forces of teeth clenching, facial tension and the repetitive body pounding of physical events cause many of the exercise induced headaches and other adverse physical or cognitive symptoms. Teeth clenching is an oral function that engages the trigeminal nerve and the muscles of mastication. The teeth clenching mechanism is a dynamic and an involuntary function occurring during physical events, stress, anger, teeth grinding, concentration and other physical and mental activities. This reflex mechanism encompasses the structures of the dental organ, muscles of mastication, and the jaw joint complex and is facilitated by the Vagus nerve. The teeth clenching reflex mechanism (TCRM) is in part responsible for the physiological attributes of strength, endurance and other physical coordinating actions. TCRM can also reduce stress, tension, or pain associated with many types of bodily injuries, exercise, physical therapy and/or rehabilitation activities and the like. Note, as a person engages in lifting a heavy object, he/she involuntarily clenches his/her teeth. These physiological attributes of the teeth clenching reflex mechanism reverse themselves out and are diminished with injury, damage, or excess wear of the jaw joint structure and the premature or early loss of (posterior) teeth.

As pointed out, the jaw joint structure is a vital component of the teeth clenching reflex mechanism and the described physical attributes. Chronic teeth clenching habits, teeth grinding disorders, stress, tension, repetitive body pounding physical activities, external impact vibration forces in the work place, and trauma will produce adverse consequences, debilitating changes, abuse and wear and tear of the jaw joint structure. These destructive episodes occurring in the jaw joint structure impair the Vagus nerve functions of the clenching reflex mechanism. The consequence of this pathology will result in the loss of endurance, strength, muscular response and more rapid fatigue with greater muscular pain during physical activities. In conjunction with headache manifestations, the jaw joint pathology produces other physical and cognitive symptoms. These symptoms may include: facial, neck, eye, ear and shoulder pain and tenderness; popping, clicking, and crepitation joint sounds when opening or closing the mouth; grinding of teeth; malocclusion (i.e., teeth do not meet together well or meet improperly); localized dental pain; ringing in the ears; increased irritability; decrease in the attention span and the physical output and other symptoms. Many of these symptoms, although familiar to the participant, are not often realized or associated with jaw joint pathology by the participant, providers of heath care, military, or the sports community.

The strenuous forces of teeth clenching, facial tension, and pounding forces of exercise, which damage the jaw joint, are transmitted through this jaw joint structure onto the base of the skull directly affecting the temporal lobe of the brain, manifesting the exercise induced temporal headache. Anatomically, the thin bony ceiling of the jaw joint structure is the thin bony floor at the inferior lateral surface of the middle cranial fossa of the skull. The middle cranial fossa is the bony structure within the skull that supports, cradles, and houses the temporal lobe of the brain.

The excessive and intensive teeth clenching, brought about by the strains of exercise, the nocturnal habits of sleep, habitual teeth grinding, and the like, will also produce damaging occlusal or bite forces against the teeth and intra-oral structures. These forces may cause sheering and fracturing of the teeth, dental restorations and related structures. Chronic teeth grinders and participants in the advanced levels of strength training often experience structural damage of the dentition.

This invention relates to the health values and the importance of exercise, sports, fitness and life style modifications. Health, fitness, personal appearance and life style modifications are the essential motivators for exercise. Obesity is the number two (2) preventable cause of death in this country. However, the trends of obesity are rapidly growing in our society, particularly in the youth who have substituted the computers for exercise and outdoor growth stimulating activities. The loss of physical education in many school systems, the high consumptions of fast foods, and baggy clothes are also other contributing factors in juvenile obesity. The epidemic trends of obesity in youth are closely followed by diabetes and also lend to the increase risk of internal organ damage, hypertension, strokes, peripheral vascular diseases and the like. Exercise has become a vital aspect in the struggles against obesity, physical rehabilitation, and disease management, with a focus on systemic exercise for conditions such as diabetes, coronary heart disease, high cholesterol, body mass index, depression, sleep apnea and others. Motivation for exercise has become a major concern in the health care delivery system.

America is aging faster than the growth rate at the younger end of the spectrum. Of the 275 million people in the US, 95 million are less than 25 years of age, 139 million are between 25 and 65 and the remaining 36 million are over 65. The over 65-age group is expected to double in the next 25 years. The elderly population increased 11 times from 1990-1994, while the non-elderly population grew just 3 times. The population of Americans age 85 and older is steadily on the rapid increase exponentially with time. Americans are living longer.

Demographic shifts and technology breakthroughs are coexisting as the elderly embrace all new technology that will improve their lifestyles including good health, fitness, and personal appearance. Coinciding with this shift and technology breakthrough are the contributions of modem dentistry. The American public is less likely to believe or accept the concept that the full denture is the destiny earmarked for the elderly. The successful dental trends in the prevention of teeth loss have improved dramatically. The baby boomer market has shown an aversion for and a remarkable reduction in the use and wear of full dentures. This reduction in the use of dentures converts to an escalation in the retention of the natural teeth in this rapidly growing elderly population. The natural aging process of teeth will show or reflect darker colors with age. These darker colors of the natural teeth are becoming less acceptable in health, fitness, personal appearance and life style modification. Many of the youth and younger Americans are also dissatisfied with the color of their teeth, which may be due to early dental injuries or other unforeseen health factors. Millions of Americans are motivated by the concept of whiter, brighter teeth projecting a healthier smile.

Teeth whitening has become the glare of attention in health, fitness, personal appearance and life style modification. Brighter, whither teeth builds self-confidence, enhances the personal appearance, and adds to the development of personal relationships and a pleasing smile. These factors compliment and enhance the exercise, health, strength, fitness and wellness programs.

U.S. Pat. Nos. 4,810,193 and 5,636,379 disclose jaw joint protective devices that provides protection for the teeth, lips, jaw, and other delicate structures of the vital cranial triad (VCT) from injury and/or for supporting the condyle of the temporomandibular joint in a relatively stable position. The VCT constitutes the condyle of the mandible, inferior lateral surface at the floor of the middle cranial fossa and the anterior temporal tympanic bone of the ear canal.

Hence, since health values that stress the importance of exercise, fitness, and life style changes are becoming increasingly necessary to people for different reasons, a need exists for simplifying yet multi-tasking procedures in order for people to achieve more personal objectives in the same period of time in order to fit the objectives into busy schedules. The present invention solves multi-tasking with regard to whitening teeth, protecting teeth, protecting and supporting the jaw joint while engaging in physical activities.

SUMMARY OF THE INVENTION

The present invention is directed to a jaw-joint therapeutic teeth whitener and protective device for protecting a wearer's lips, tongue, teeth, VCT, and other oral structures within the full maxillary and mandibular arches of the mouth, and jaw-joint structures by repositioning the condyle in relationship to the fossa. The device is composed of a) a U-shaped base having a bilateral posterior dental region and an anterior dental region with integrated maxillary and mandibular components where the components are adapted for securement within the full maxillary and mandibular arches of the mouth, whereby the mandibular component is offset downwardly and forwardly from the maxillary component so that the mandible is set in a secure and protruded position;

b) an occlusal impact chamber in the mandibular and maxillary dental regions of the base filled with a resilient material for absorption and dissipation of shock away from the teeth, jaw joint, and related facial structures;

c) the maxillary flange component is composed of the labial and buccal walls projecting upwardly from the base forming with the base and providing for seating a custom fitting bleaching strip, used during the custom fitting procedure, which creates on the inside or dental surface of the labial and buccal walls an inverse bleaching cavity for containing and retaining a whitening agent;

d) the mandibular flange component composed of the labial and buccal walls projecting downwardly from the base forming with the base and providing for seating a custom fitting bleaching strip, used during the custom fitting procedure, and protecting the mandibular teeth, and a reinforced anterior dental region with a deep labial flange to support and guide the mandible into the engineered functionally prognathic position creating the force attenuating recoil space of the jaw-joint and lingual lock of the lingual wall in the anterior dental region of the device projecting downwardly from the base forming with the base and providing for stability and support against forces driving the mandible back from the prognathic position while supporting and strengthening anterior teeth;

e) custom fitting bleaching strips that are composed of an independent and separate elastomeric material that conforms to the U-shaped articulated mandibular and maxillary buccal and labial walls of the device, which creates on the inside or dental surface of the labial and buccal walls of the maxillary and mandibular components an inverse bleaching cavity for containing and retaining a whitening agent, f) an articulating rim in the lingual wall of the maxillary component in the anterior dental region of the device that eliminates the need for a palatal component, so that the tongue of the wearer can be placed against the lingual surface of the anterior maxillary teeth for articulating speech; and g) a functional air-way passage from canine to canine in the anterior of the integrated components to facilitate breathing, expectorating, and speaking.

The present invention also relates to a method of fitting in situ by the wearer of the above mentioned jaw-joint protective, exerciser bleaching device by first heating the device in hot water to a temperature greater than body temperature to soften certain portions of the device with bleaching strips in place and immediately placing the device in the wearer's mouth and the wearer biting down on the base so as to make teeth impressions in the base while sucking with added finger pressure against the upper and lower lips, molding the dental surface of the maxillary and mandibular labial and buccal flanges (walls). Then, the device is removed from the user's mouth and then cooled, whereby the device hardens to a rigid form maintaining the impression of the teeth, arch form and bleaching cavity of the wearer thereby customizing the device. The bleaching strips are removed and discarded.

BRIEF DESCRIPTION OF THE DRAWINGS

FIG. 1 is a sectional frontal view of the mouth showing the airway opening or expectorant orifice in the exercise whitener device.

FIG. 2 is a partial side view of the head showing the components of the functional change in the temporomandibular joint complex with the exercise whitener device in place.

FIG. 3 is a frontal view of the exercise whitener device showing the adjustable labial knotch and airway space.

FIG. 4 is a top plan view of the device showing the articulating rim, bleaching strip, and no palatal component.

DETAILED DESCRIPTION OF THE INVENTION

Figure 5:
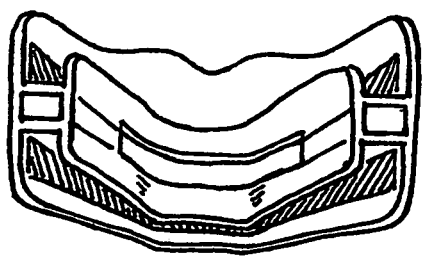
FIG. 5 is a rear view of the exercise whitener device, looking from the rear to the front of the device showing the bleaching strips in place.

It has been surprisingly found that a mouth guard appliance can achieve multi-tasking by not only providing protection to the oral cavity, jaw joint, and enhancing the teeth clenching reflex mechanism (TCRM) but also can brighten and whiten teeth at the same time.

In accordance with the present invention, the exercise whitener device combines the utilities of an intra-oral impact appliance, (i.e., the stress, anxiety, grinding attenuation and impact absorption intra-oral appliances) with the teeth whitening or teeth bleaching trays system.

The present invention allows the user to engage in the activities of exercise, rapid acceleration devices, physical therapy, sports, military maneuvers, sleep apnea reduction, and the like while bleaching or whitening the teeth effectively at the same time. The exercise whitener will also enhance the physical attributes of the TCRM, producing the notable increase in strength, energy and endurance with the reduction of pain and stress of exercise during use. It will allow the user to get more physical benefits out of exercise in the least amount of time.

The application of this invention is a great motivator for exercise in disease management, obesity, physical therapy, strength training, health, fitness, and wellness. This teeth whitening and strength enhancing intra-oral appliance can also be used for the physical science and impact of sports. This invention achieves the aesthetics of a brighter, whiter smile with the appeal of a stronger, more fit and healthier body. With the anterior opening, the repositioning of the lower jaw and the increase in the size or volume of glottis airway space, this appliance will reduce snoring in a large user population while whitening the teeth. This enhances interpersonal relationships with the significant other by reducing sleep apnea, promotes more restful sleep, and builds self-confidence with a brighter whiter smile.

It has been found that the exerciser, jaw-joint protective and teeth whitening device composed of two different types of materials for different purposes can be used by a wearer to provide protection not only to the oral cavity but also to the vital cranial triad (VCT) and component structures and provide teeth whitening during wear. The VCT broadens the defined structural component of what is commonly known as the temporomandibular joint. The invention supports the mandible and condyle in a relatively fixed position thereby stabilizing the lower jaw and VCT during head contact, exercise, physical therapy, teeth grinding and sleep apnea activities and/or to permit the components of any VCT disorders to be realigned reducing load forces to the jaw joint during head contact and/or physical activities or bodily jarring forces during selective teeth whitening procedures.

This device is simple in structure and fitting components but it is strong in purpose for achieving the maximum protection for the delicate bones and structures of the base of the skull, the jaw joint and oral cavity and providing the bleaching cavity for discretionary teeth whitening activities. The simple exerciser, jaw-joint protective and teeth whitening device of the present invention can be simply adapted to a wearer's mouth perfectly in situ by the wearer heating the device in water and then placing it in his/her mouth and biting down on the device so as to make an impression of the occlusal surfaces of the teeth in the occlusal impact surface of the dental arches and molding the dental surface of the labial and buccal walls of the device to create the custom fitted gel cavity which will set up in a few seconds.

Figure 6:
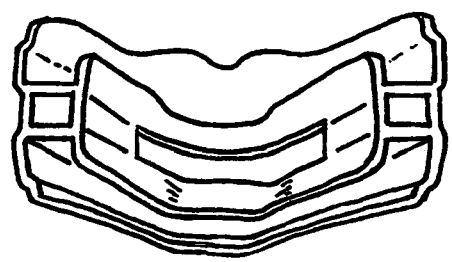
FIG. 6 is a rear view of the exercise whitener device, looking from the rear to the front of the device showing the formation of the bleaching cavities.
Figure 7:
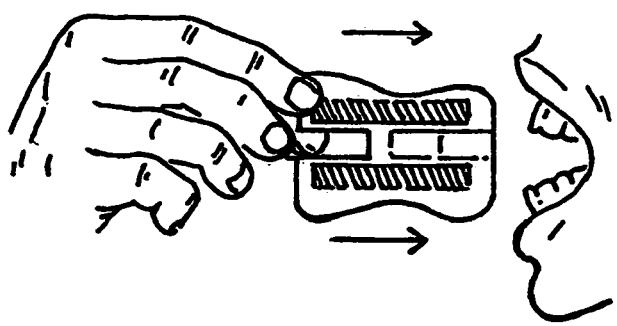
FIG. 7 is a side view of the exercise whitener device with the bleaching strips in place being placed in a user's mouth for fitting.
Figure 8:
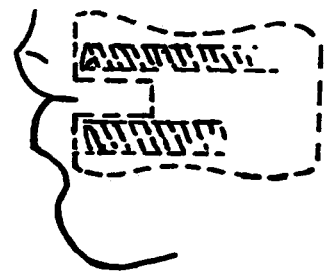
FIG. 8 is a view showing the user biting down into the maxillary and mandibular channels while molding the buccal and labial walls of the device for in situ fitting.
Figure 9:
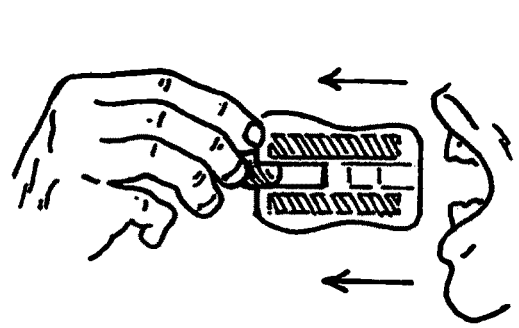
FIG. 9 is a view showing the removal of the device for cooling.

The present invention has integrated base of the double arches forming upper and lower bite channels of the exercise whitener, which are composed of upper and lower labial and buccal walls and upper and lower lingual walls, (see FIG. 5). The labial and buccal walls are the beacons of this invention. The outside surfaces of the labial and buccal walls will be in contact with the lips and cheeks. The inside surface of the labial and buccal walls will contact and cover the front surface of the teeth and parts of the gums (gingiva), (see FIG. 1). For the ease of fitting during the boil and bite custom fitting process only, the custom fitting bleaching strips are used (see FIG. 5). The custom fitting bleaching strips are made from a material that is more stable and less responsive in heat than the labial and buccal flange (wall) material. In the design of the boil and bite fitting of the appliance, the placement of the custom fitting bleaching strips is essential. The custom fitting bleaching strips are seated between the inside surface of the upper and lower labial and buccal walls of the device and the facial or outside surface of the teeth, (see FIG. 5). This insures the formation of the bleaching cavity or negative impression, (see FIG. 6), on the inside surface of the upper and lower labial and buccal walls during the fitting process. After the fitting procedure the custom fitting bleaching strips are discarded (see FIGS. 10 & 11). The bleaching cavity, formed on the inside surface of the upper and lower labial and buccal walls, holds and retains the whitening agent against the front or labial and buccal surfaces of the teeth to maximize the whitening proficiency during use. In another embodiment, the user may also opt to mold the custom fitting bleaching strips directly for one or more teeth to provide a more detailed or specific whitening pattern. In this embodiment, buccal pads are placed directly onto each of the user's teeth that are to be bleached prior to the boiling and biting of the device. This embodiment enables the user to either focus in on a single tooth or as many teeth as desired for treatment up to the user's entire mouth. These fitting procedure embodiments have created a custom fitted mouth guard appliance in combination with custom fitted bleaching or whitening trays. The whitening agent can be in the form of a strip, paste, gel, or solution and can come in different strengths and flavors. The whitening agents may be used discretionarily with the exercise whitener device.

In order to understand and appreciate the structural features and benefits of the exerciser, jaw-joint protective and teeth whitening device of the present invention, a brief review of the anatomy for which the device protects and functions will be described.

FIG. 2 shows the functionally protected position of the VCT complex and the bleaching gel cavity against labial and buccal surfaces of the teeth with the device in place. The area of the mouth affected by the bleaching gel cavity of the device is the facial surfaces of the mandibular and maxillary teeth. The areas of the head, protected by the device are the oral cavity or mouth that is composed of the teeth that sit in a rigidly fixed upper jaw 2 and a moveable lower jaw 1 which is movably connected to the cranium at the temporomandibular joint (TMJ). The joint is defined by two primary bones, the mandibular bone 1, which articulates with the temporal bone as a ball (condyle 2) and socket (glenoid fossa 3) joint.

Referring to either side of the human head, the temporal bone houses the very thin and delicate glenoid fossa 3 (laying on the bone of this fossa is the temporal lobe of the brain) which is the socket of the temporomandibular joint. The articular eminence 5 forms the anterior component of the fossa. Positioned between the condyle 2, the most posterior ball-like structure of the mandible, and the fossa 3 is the soft tissue of the meniscus (cartilage or disc) of the TMJ. The auditory meatus 6, temporal tympanic bones 7 *a, b, c.*, and post glenoid process 8 are also shown. The post glenoid process 8 and the anterior superior surface of the temporal tympanic bones 7*a,b,c* unite at 9. Housed in the temporal tympanic bones 7*a,b,c* are the auditory and balance mechanisms, among other vital structures. Medially and inferiorly to the medial surface of the condyle 2 is the inferior surface of the petrous temporal bone porting a complex of cranial nerves trunks as they exit from the base of the brain and housing the internal carotid artery which is the primary supply of blood to the brain.

In the case of internal derangement including of teeth clenching, facial tension and the repetitive body pounding of physical exercise, fitness, strength, and physical training, rehabilitation, sleep apnea, teeth grinding, and sports related injuries of the VCT, the aberrant forces from these events tap, abruptly slam or damagingly compress the condyle against the delicate structures of the VCT. These load forces will produce radiographically discernible fractures associated with concussions and structural changes of the delicate bones and contusions, compressions, or hemiations of the soft tissue of the VCT. Thus, it should come as no surprise that athletes and persons suffering from VCT injuries or changes often present cognitive symptoms reflecting neurologic and circulatory deficit. These cognitive symptoms may include migraine-like headache, earache, facial pain, bloodshot eyes, exercise induced headaches, photosensitivity, muscle weakness, pain and numbness of extremities, vomiting, vertigo, impaired speech, raspy voices, and decrease in hearing abilities among other clinical symptoms.

In conjunction with the aforementioned structures, the mandibular and maxillary dentition and gingiva, as well as, the tongue, lips, and other oral structures must be protected during exercise, physical rehabilitation, sports activities, military maneuvers, and during external vibration activities (such as air hammer drilling, rotary air craft vibration, etc).

In accordance with the present invention, the device (FIGS. 5 and 6) employs a design to prevent and overcome dental and jaw-joint problems typically as a result of contact sports while motivating participators to engage in these activities with teeth whitening enhancement. The device is composed of a reinforced anterior dental region and bilateral posterior dental regions where the maxillary and mandibular teeth are functionally seated having labial border 10, lingual border 15, buccal border 11, articular rim 12, lingual lock 13 and bleaching cavities 17*a* and *b*. The upper and lower bleaching strips 17*a* and *b* create the bleaching cavities 17*a* and *b*. The exerciser, jaw-joint protective teeth whitener repositions the lower jaw and condyle in a downward and forward position relative to the normal or centric position of the condyle 2 (see FIG. 2). In other words, the lower jaw is extended in a prognathic position. This device also establishes an occlusal offset that positions the incisal surfaces of the mandibular incisal teeth downward and forward in relationship to the maxillary incisal teeth. This device also establishes an occlusal lock that creates a relationship between the upper and lower teeth in such a way as to minimize lateral, adverse, and relative movement during contact. In other words, the device maximizes jaw stability and locks the lower jaw in an extended position. The downward and forward position of the lower jaw in conjunction with the device creates the anterior functional freeway space 14 and force attenuation space 1 of the jaw joint. This device also establishes a well-defined indentation or cavity 17*a* and *b* in the dental surface of the maxillary and mandibular labial and buccal walls of the device to provide an effective cavity to hold and retain whitening agents for the efficient teeth whitening procedures of the maxillary and mandibular dentition.

A palatal portion commonly found in conventional mouthpieces normally ending just before the soft palate of the mouth is absent from this jaw-joint protective device because of the engineered design for strength in the mandibular and maxillary posterior bite components of this device; moreover, it would impair articulated speech and in many cases elicited a gag reflex. The. labial-buccal borders 10 and 11 are present and positioned in the mucco-buccal fold of the mouth avoiding impingement of the labial frenum and posterior muscle attachments. The adjustable labial knotch 18 enables the wearer to place the labial flange high into the labial fold of the mouth without cutting or damaging the labial frenum while maintaining the integrity of the bleaching strip 16 and the newly formed bleaching cavity 17.

FIG. 4, the top plain view, shows that the lingual surface is reinforced by the articular rim 12 behind the maxillary anterior teeth from canine to canine: likewise, the labial-buccal maxillary flange is reinforced by the bleaching strip 19.

FIG. 5, the rear view, shows in accordance with the present invention, the custom fitting bleaching strips 16*a* and *b* are composed of an independent and separate hard elastomeric material that conforms to the U-shaped articulated mandibular and maxillary components of the device. The bleaching strips 16a and b of this invention are not easily affected by heat and are used only for the custom fitting procedure and are then removed and discarded. The rigid elastomeric material bleaching strips 16a and b run primarily the length of the inside or dental surface of the maxillary and mandibular labial and buccal walls but are shorter and narrower than the length and height of the maxillary and mandibular labial and buccal walls. The bleaching strip components are seated from the base of the maxillary channel between the inside surface or dental surface of the labial and buccal walls and the labial and buccal (facial) surfaces of the maxillary teeth. In the lower jaw, the bleaching strip component is seated from the base of the mandibular channel between the inside surface or dental surface of the labial and buccal walls and the labial and buccal (facial) surface of the mandibular teeth. The bleaching strip components also may be altered for the specific fit of one or more teeth to create the bleaching cavity for a specific bleaching pattern as needed. In this embodiment, pads are placed directly onto each of the teeth that is to be bleached. These pads are also made of a rigid material that will not harm the tooth or teeth that is strong enough to make the desired impression in the device as needed. When the buccal pads are placed directly onto the facial surface of the tooth/teeth just prior to the boil and bite fitting, these pads or pad will produce an indentation on the tooth or teeth surface of anterior and buccal flanges of the device, shown in FIG. 6. These indentations are the sites for the placement of the whitening medium.

When the device is placed in the mouth with the mandible placed in the functionally protruded position, the mandibular and maxillary units being integrated into one unit protects the oral cavity and positions the condyle of the VCT into a protective and exaggerated position that also enhances the function of the TCRM. The engineered mandibular jaw placement is governed by the device, the kinesiological functional physiology, the condyle-fossa physiology, the force attenuation space, and the functional free-way space.

FIGS. 1. and 2 show the comparison of the design of the exerciser, jaw-joint protective teeth whitener device in the mouth in FIG. 2 is such that the upper and lower dental arches are held in a spaced-apart position of desired dimensions with an airway 14 (or saliva orifice) so that the participant wearing the device can readily breathe or expectorate or talk, depending on the activity. This functional airway space 14 is in the anterior sextant component of the mouth that is composed of an oversized space that can be extended from premolar to premolar or canine to canine. The anterior free-way space 14 also can be used as a means to grasp the device, which enables the jaw-joint protective appliance to be removed from an injured or unconscious participant. In FIG. 2, number 1 shows the force attenuation space that is the acquired safety margin in the jaw joint space gained by the design of the device when properly placed in the mouth and the mandibular and maxillary bleaching cavities 19a and b are formed during the fitting procedures.

FIG. 5 shows the lingual view of the maxillary arch that has a thicker, tapered, depressed portion in the anterior region that defines an articulating rim 12 which aids in the production of speech and gives support to the lingual surface of the anterior teeth. This articulating rim 12 combined with the anterior free way air space 14 enables the wearer to speak, to breathe actively and passively through the mouth while wearing the jaw-joint protective and whitening appliance. The down and forward positioning of the mandible physiologically increases the volume of the glottis airway space. This enhances the oxygen exchange with the lungs. With this improved functional airway space 14, if the participant should become unconscious, a patent airway is always maintained.

Figure 10:
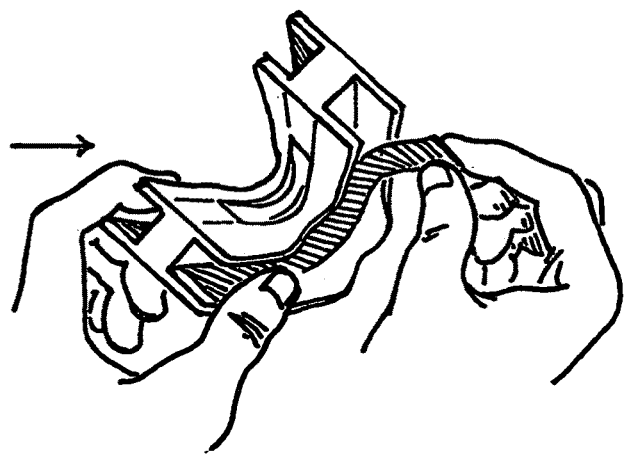
FIG. 10 is a view showing the removal and discarding of the bleaching strip from the maxillary component of the device after cooling of the device.
Figure 11:
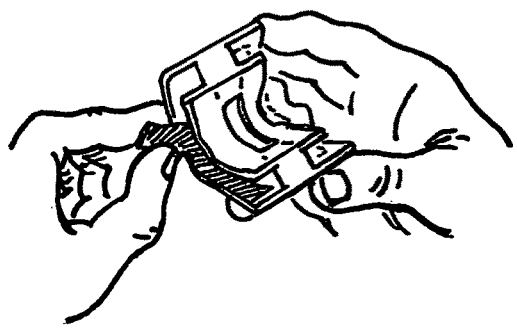
FIG. 11 is a view showing the removal and discarding of the bleaching strip from the mandibular component of the device after cooling of the device.
Figure 12:
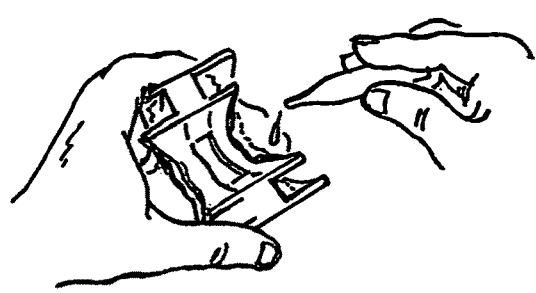
FIG. 12 is a view showing the adding of a whitening agent to the newly formed bleaching cavities of the device for use by the wearer.
Figure 13:
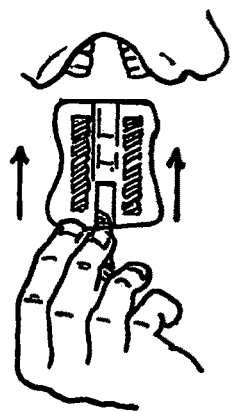
FIG. 13 is a view showing the re-insertion of the whitening device with the bleaching agent in place.

The present invention also relates to a method of fitting in situ by the wearer of the above-mentioned jaw-joint protective and whitening device (FIGS. 7-14). Either the user or someone assisting him (or her), for instance in the case of a minor child, can heat the device in hot water to a temperature greater than body temperature but less than or equal to 100° C. to soften certain portions of the device, as engineered, and immediately placing it in the wearer's mouth (see FIG. 7). The wearer with the custom fitting bleaching strip in place, then bites down on the base of the device (FIG. 8) so as to make teeth impressions in the base and applies suction and pressure with, e.g., the tongue, fingers, lips, oral musculature, to create a good firm fit. The wearer also applies suction and pressure with the use of fingers, lips, oral musculature, to create a good firm fit of the labial and buccal flanges against the custom fitting bleaching strips. Then the device is removed from the mouth and cooled down (FIG. 9) whereby the device hardens to a rigid form. The cooling step only takes a few seconds. After cooling, the custom fitting bleaching strips are removed and discarded (FIGS. 10 and 11). The whitening agent is then placed in the bleaching channels of the device (FIG. 12) and the device is then placed back in the mouth (FIG. 13) with the user's head in a tilted down position so as not to disturb the whitening agent. This device can be used just as a teeth whitener or brightener appliance during a physical activity, sleep, or just relaxing.

Figure 14:
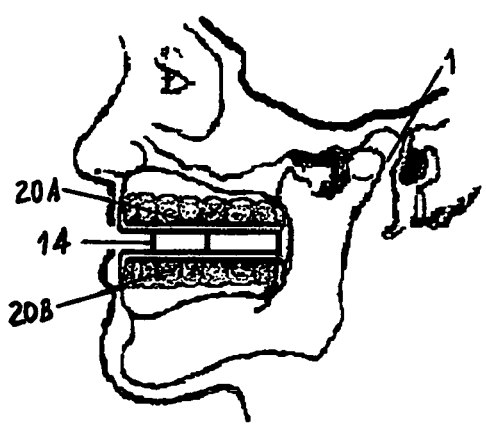
FIG. 14 is a view showing the whitening device with the whitening agent in place in the mouth creating the safety margin in the jaw joint space to reduce lower jaw impact concussions.
Figure 15A:
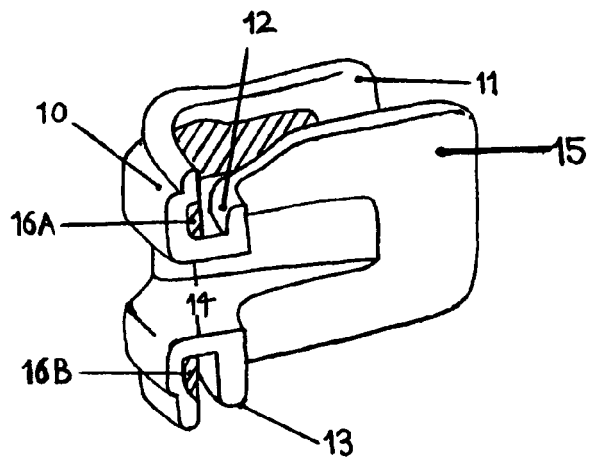
FIG. 15a is a mid-sagittal view of the mouth guard with the bleaching strip in place and that the lower jaw is open and anterior to the upper jaw.
Figure 15B:
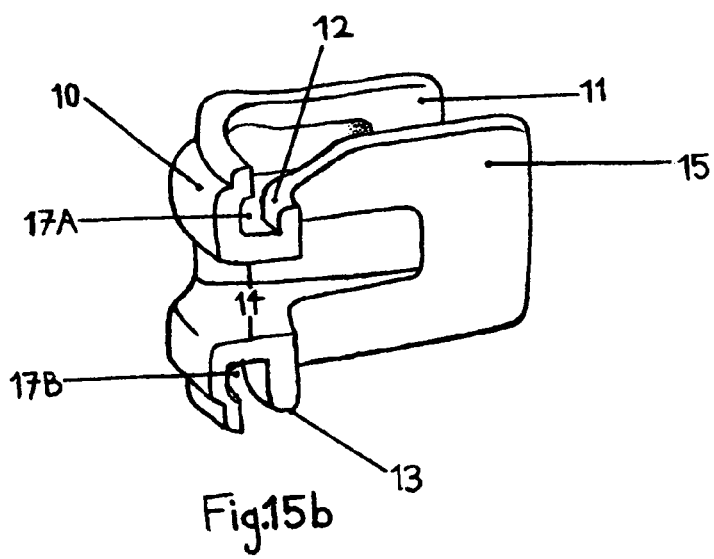
FIG. 15b is a mid-sagittal view of the mouth guard with the bleaching strip removed showing the bleaching cavity in which whitening gel can be placed.

FIG. 14 shows the jaw joint stabilizing and whitening device in place with bleaching strips removed and whitening agent placed in the bleaching canals and condyle displaced down and forward away from the glenoid fossa creating a safety margin against lower jaw impact concussions.

In the device, the reinforced anterior and posterior dental regions of the maxillary and mandibular components are composed of a resilient thermoplastic material for dissipation and absorption of shock imposed upon the wearer's head during sporting or exercising activities. In the portions of the device where the teeth surfaces are in direct contact with the device, the device is made of thermoplastic material that softens when heated in water above body temperature and rigidly stiffens when cooled so that the device can be perfectly fitted in situ. The remainder of the device is made of a rigid elastomeric material that maintains its rigidity when heated in water above body temperature.

This device and the custom fitting bleaching strip are mass-produced in various sizes to fit different prospective users such as men, women, and children. The normal sizes are large, medium, or small. The device can be produced, for example, by injection molding or machine stamping techniques that are well known in the art.

The occlusal bite channel and wall material of the device are normally made of a thermoplastic material such as ethylene vinyl acetate that can withstand pressure, is easily molded, and is inert to the mouth chemistry of the person wearing it. This thermoplastic material must be able to soften when heated above body temperature but below or equal to 100° C. and yet to harden again when it is cooled down outside of the user's mouth for molding to the impression of the wearer's mouth. Natural rubber can also be used for producing the jaw-joint protector and whitener device of the present invention which rubber must be heavy duty, non-toxic, and inert, which would be well known to a person in this art.

The resilient material that is used as the primary foundation for the framework and shape for the reinforced anterior dental region in the maxillary and mandibular components and posterior component bilaterally and the custom fitting bleaching strips, would normally be prepared from a different material from that of the rest of the device that serves the function of strength for protection. The material is normally a thermoplastic material such as an elastomer. An example of this elastomer is a Kraton material. Natural rubber can also be used for producing these resilient portions of the jaw-joint protector of the present invention which rubber must be heavy duty, non-toxic, and inert and stable to the heating temperature of this device, which would be well known to a person in this art. Other materials for the device that meet the specifications of the American Dental Association for intra-oral use would be known to a person in the art.

Many advantages of the exerciser, jaw-joint protective, teeth whitener device of the present invention exist over the conventional mouth guards. The present invention absorbs shock, traumatic vibrations and impacts to the head forces, displaces the condyle in a downward and forward position creating the force attenuation space dissipating and absorbing these load forces previously directed to the VCT, protects maxillary and mandibular dentition while whitening the teeth. The adjustable labial knotch prevents injuries of the attached labial freneum while allowing the labial flange to seat higher into the labial fold of the mouth for greater fitting and labial adaptation and greater definition of the bleaching cavity allowing for greater retention of the whitening agent. The exerciser, jaw-joint protective, teeth whitener device also eliminates compression of the disc and condyle-fossa space of the TMJ with trauma to the head, provides greater stability against traumatic displacement of the lower jaw onto the delicate bones in the head, decreases trauma to the anterior components of the tongue, decreases the incidence of lip injuries "the teeth through the lip syndrome", and enhances the clenching mechanism while allowing the participant to functionally breath through the mouth.

The continued wearing of this device of the present invention promotes healing of an injured condyle-fossa complex and other facial structures while the participant actively engages in sports, exercise, physical therapy, traumatic vibration force induced environments, sleep or at rest. Since articulated speech can be performed and nutrients passed through the air way space when the device is being worn by a person and is comfortable in the mouth, it is conceivable that this device can be used in arch stabilization and repair of other facial and jaw fractures; therefore, users of the device can use the device as a medical appliance. In other words, the exerciser, jaw-joint protective, teeth whitener device of the present invention facilitates remodeling and repair of injured condyle-fossa relationship, VCT components and other facial bones. This device also increases functional physical output and strength of the athlete by repositioning the condyle away from the injured structures in the VCT; this is another incentive why it can be worn either while a wearer is actively participating in a sport or just performing normal everyday activities or being at rest. This device can also be used to increase palatal airflow patterns during sleep and thereby reduce snoring. The wearing of this device will also mitigate the adverse forces associated with clenching and grinding of the teeth during sleep.

While the invention has been described with respect to specific embodiments, it should be understood that the invention should not be limited thereto and that many variations and modifications are possible without departing from the spirit and scope of the invention.

What is claimed:

1. A jaw joint therapeutic teeth whitening and protective device for protecting a wearer's lips, teeth, and other delicate structures of the head including the vital cranial triad (VCT), which is comprised of the bones and tissue structures found in the temporomandibular joint, temporal tympanic bone of the ear canal, and the inferior lateral surface of the petrous temporal bone at the floor of the middle cranial fossa and related structures within the full maxillary and mandibular arches of the mouth, comprising a) a U-shaped base having a bilateral posterior dental region and anterior dental region with an integral maxillary component and a mandibular component, the maxillary component and mandibular component are adapted for securement within the full maxillary and mandibular arches of the mouth, whereby the mandibular component is offset downwardly and forwardly from the maxillary component to create an anterior airway space, the mandibular component being configured to cause the mandible to be in a protruding-like position relative to the maxillary component, b) a full arch occlusal impact chamber in a dental region of the maxillary and mandibular components of the base, the impact chamber comprises a resilient material for dissipation and absorption of shock imposed upon the mandible, maxilla, head, jaw joint and facial structures, c) the maxillary component comprises labial and buccal walls projecting upwardly from the base and forming with the base a maxillary channel for seating and protecting the maxillary teeth when received therein, wherein the maxillary component further comprises a lingual wall projecting upwardly from the base for contacting the lingual side of the maxillary anterior teeth, the lingual wall forming a maxillary incisal lock and having an articulating rim, wherein a height of the articulating rim is sufficiently small enough to cause a tongue posture against the lingual surface of the maxillary anterior teeth that promotes articulation and speech when the device is in use, and the height of the articulating rim is sufficient to maintain the stability of the maxillary incisal lock and maintain the support and strength for the incisal teeth, d) the mandibular component comprises labial and buccal walls projecting downwardly and forwardly from the base and forming with the base a mandibular channel configured for seating and protecting the mandibular teeth when received therein, wherein the mandibular component further comprises:

a reinforced anterior dental region with a deep labial flange to support and guide the mandible into a functionally prognathic position that creates a force attenuating recoil space of the jaw-joint, and a lingual lock disposed in an anterior dental region and a posterior dental region of the device configured for forming a mandibular incisal lock which extends downwardly from the base to engage the lingual side of the mandibular teeth to support and maintain the prognathic position while supporting and strengthening the mandibular anterior teeth, e) bleach cavity forming strips that comprise an elastomeric material formed separately from the remainder of the device and conforming to the u-shaped articulated mandibular and maxillary buccal and labial walls of the device, wherein:

during a boil and bite fitting procedure applied to the device and said strips, an inverse cavity configured for retaining a whitening agent against a facial surface of mandibular teeth and/or maxillary teeth is formed by removing the bleach cavity forming strips from the u-shaped articulated mandibular and maxillary buccal and labial walls of the device, a geometry of the inverse cavity is defined by a geometry of the bleach cavity forming strips, and the cavity forming strips comprise a material having a rigidity that is insubstantially affected by temperatures sustained during the boil and bite fitting procedure, f) an anterior airway space adapted to extend from canine to canine in the anterior region of the device is large enough to create and enhance greater active and passive airflow, expectorating, speech and articulation, and wherein a more heat stable elastomeric material of the anterior dental regions of the maxillary and mandibular components and the posterior components bilaterally maintain the framework and shape of the device and dissipate and absorb shock imposed upon the wearer's head and the remainder of the device is made of a more heat sensitive thermoplastic material that softens when heated to a temperature greater than body temperature but less than or equal to 100° C. and rigidly stiffens when cooled so that the device can be perfectly fitted in situ.

2. The device of claim 1, wherein the resilient material is a thermoplastic elastomer.

3. The device of claim 1, wherein the anterior airway comprises an expectorant orifice or an articulation chamber.

4. The device in claim 1, wherein different materials of the device will maintain the mandibular and maxillary dental arches locked in a bite surface that stabilizes the jaw against lateral and traumatic jaw displacement made of a common boil and bite dental material and having a secondary material which maintains the mandibular prognathic repositioning of the lower jaw and structural integrity of the device during the boil and bite phase of fitting and eliminating the need for a palatal component of conventional mouthguards.

5. The device of claim 1, wherein the bleach cavity forming strips comprise a first and second pad that are directly placed onto the facial surface of at least one tooth, respectively, prior to the boiling and biting process, whereby the first pad and second pad provide separate indentations for a custom fitting chamber for each surface of a tooth.

6. The device of claim 1, wherein an adjustable labial knotch prevents injuries of the attached labial freneum while allowing the labial flange to seat higher into the labial fold of the mouth for greater fitting and labial adaptation and greater definition of the bleaching cavity allowing for greater retention of the whitening agent.

7. A method of treating a jaw-joint disorder and other facial fractures by a person having such a disorder comprising wearing the device of claim 1 when participating in athletic activity, physical therapy, or when in need to correct such disorder, wherein wearing the device holds the temporomandibular joint and jaw components in a stable and functional position for a sufficient time period in order to afford protection, stability, and healing thereof.

8. A method for supporting and enhancing the teeth clenching mechanism and incorporating bodily strength and balance during physical rehabilitation, or exercise while whitening the teeth comprising wearing the device of claim 1 while participating in rehabilitation or exercise.

9. A method of fitting in situ the device of claim 1 in the mouth of a user comprising heating the device in hot water to a temperature greater than body temperature but less than or equal to 100° C. to soften certain portions of the device, immediately placing the device in the wearer's mouth, the wearer biting down on the base so as to make teeth impressions in the base while the wearer is applying suction and pressure to the device with the tongue, lips, and oral musculature and further molding the device with corresponding fingers and lip pressures, removing the device from the wearer's mouth, cooling the device down whereby the device hardens to a rigid form, and removing the bleach cavity forming strips from the device and discarding them, whereby the device is now customized to the wearer's mouth.

10. A method of treating sleep disorders of snoring, grinding and clenching of teeth, and sleep apnea while whitening the teeth comprising wearing the device of claim 1 while sleeping.

11. A jaw joint therapeutic teeth whitening and protective device for use in a user's mouth, comprising:

a) a U-shaped base having upper and lower occlusal surface areas spaced from one another and against which said maxillary and mandible teeth will rest;

b) an occlusal impact chamber disposed in said base between and bordered by said upper and lower occlusal surface areas, said occlusal impact chamber comprising a hard resilient material for dissipation and absorption of shock imposed upon the mandible, maxilla, head, jaw joint and facial structures;

c) a maxillary component comprising labial and buccal walls extending upwardly from an anterior side of the base and a lingual wall extending upwardly from a posterior side of the base, said labial, buccal and lingual walls and said upper occlusal surface area of said base forming an upper channel capable of receiving and protecting said maxillary teeth therein;

d) a mandibular component comprising labial and buccal walls extending downwardly from an anterior side of the base and a lingual wall extending downwardly from a posterior side of the base, said labial, buccal and lingual walls and said lower occlusal surface area of said base forming a lower channel capable of receiving and protecting said mandibular teeth therein;

e) an air passage disposed between said upper and lower occlusal surfaces surface areas having an opening of sufficient size to allow breathing and speaking by the user;

f) said upper and lower channels of said maxillary and mandibular components being configured to position the mandible of the user into a prognathic position so as to create and maintain a force attenuating recoil space of the jaw-joint;

g) at least one bleach cavity forming strip formed separate from a remainder of the device, said strip having a desired shape and is configured for placement along said buccal and labial walls within said upper and lower channels at a desired location, wherein said cavity forming strip comprises a material that will soften less in response to heat than a material of said buccal and labial walls within said upper and lower channels, wherein during a custom fitting procedure for the device, by remaining more rigid than the buccal and labial walls when exposed to heat, said strip is capable of forming a bleaching cavity in said buccal and labial walls corresponding to said desired shape at said desired location, and which bleaching cavity is suitable for receiving a whitener agent upon removal of said strip; and h) wherein said buccal and labial walls within said upper and lower channels comprise an elastomeric material capable of softening sufficiently to allow the formation of said bleaching cavity therein during said fitting process when heated to a fitting temperature sufficient for creating said bleaching cavity and which stiffens rigidly to maintain said bleaching cavity when cooled, and wherein said bleach cavity forming strip is made of a material that will maintain its shape when heated to said fitting temperature so as to be capable of forming said bleaching cavity.

12. The device of claim 11 wherein said desired shape comprises a shape of the labial side of an individual tooth.

13. The device of claim 11, wherein said desired shape can include a shape of the labial side of several individual teeth.

14. A customized protective mouth guard having bleaching cavities, the mouth guard being custom formed in-situ in a user's mouth by a boil and bite fitting process, the mouth guard comprising:
   a) a unitary U-shaped base formed of a resilient thermoplastic material that softens when heated in water between body temperature and 100° C., the base having an upper occlusal surface configured for maxillary teeth and a lower occlusal surface configured for mandible teeth, the upper occlusal surface comprises an upper channel including an upper bleaching cavity and the lower occlusal surface comprises a lower channel including a lower bleaching cavity,
   b) a maxillary component formed of a rigid thermoplastic material that softens when heated in water above body temperature and below 100° C., the maxillary component comprising protection walls including labial and buccal walls extending upwardly from an anterior side of the base and a lingual wall extending upwardly from a posterior side of the base;
   c) a mandibular component formed of a rigid thermoplastic material that softens when heated in water above body temperature and below 100° C., the mandibular component comprising protection walls including labial and buccal walls extending downwardly from an anterior side of the base and a lingual wall extending downwardly from a posterior side of the base,
   d) an upper and a lower sacrificial bleaching strip formed of a hard elastomeric material having a hardness that is insubstantially affected by boiling water during the boil and bite fitting process, the upper and lower sacrificial bleaching strips having a size and shape that defines the upper bleaching cavity and the lower bleaching cavity, respectively,
   e) wherein, during the boil and bite fitting process, the upper and lower bleaching cavities are formed by removing the upper and lower sacrificial bleaching strips, respectively.

15. The mouth guard of claim 14, wherein, during the boil and bite fitting process, the upper and lower bleach cavities are formed by applying indentation pressure to the upper and lower channels via facial surfaces of the mandibular teeth and maxillary teeth, respectively.

16. The mouth guard of claim 15, wherein, during the boil and bite fitting process, a custom geometry is formed in at least one of the upper bleaching cavity and lower bleaching cavity by applying indentation pressure via at least one sacrificial buccal pad disposed on a facial surface of the mandibular teeth and/or maxillary teeth.

17. A method of forming a mouth guard in-situ in an end users mouth, comprising:
   providing a mouth guard, the mouth guard comprising:
      a) a unitary U-shaped base comprising an upper occlusal surface and a lower occlusal surface, the upper occlusal surface including an upper channel and the lower occlusal surface including a lower channel;
      b) a maxillary component comprising protection walls including labial and buccal walls extending upwardly from an anterior side of the base and a lingual wall extending upwardly from a posterior side of the base;
      c) a mandibular component comprising protection walls including labial and buccal walls extending downwardly from an anterior side of the base and a lingual wall extending downwardly from a posterior side of the base;
      d) upper and lower sacrificial bleaching strips having a size and shape configured to define an upper bleaching cavity and a lower bleaching cavity in the upper channel and the lower channel, respectively;
   heating the mouth guard in hot water to a temperature greater than body temperature but less than or equal to about 100° C.;
   placing, after the heating step, the mouth guard in an end user's mouth;
   biting down, after the placing step, on the mouth guard thereby making teeth impressions of the end user's mouth, wherein the upper and lower sacrificial bleaching strips will form the upper and lower bleaching cavities, respectively;
   cooling the mouth guard down such that the mouth guard hardens to a substantially rigid form; and
   removing, after cooling step, the upper and lower sacrificial bleaching strips from the upper and lower bleaching cavities, respectively.

18. The method of claim 17, further comprising:
   applying, by the end user, suction and pressure to the mouth guard with the tongue, lips, and oral musculature; and
   applying, by the end user, pressure to the mouth guard via finger pressure and lip pressure.

19. The method of claim 18, wherein:
   the unitary U-shaped base is formed of a resilient thermoplastic material that softens when heated in water between body temperature and 100° C.;
   the maxillary component is formed of a rigid thermoplastic material that softens when heated in water above body temperature and below 100° C.;
   the mandibular component is formed of a rigid thermoplastic material that softens when heated in water above body temperature and below 100° C.; and
   the upper and a lower sacrificial bleaching strips are formed of a hard elastomeric material having a hardness that is insubstantially affected when heated in water above body temperature and below 100° C.

* * * * *